United States Patent
Minnifield

(10) Patent No.: US 10,433,770 B1
(45) Date of Patent: Oct. 8, 2019

(54) MEASUREMENT DEVICE FOR ASSESSING KNEE MOVEMENT

(71) Applicant: Measuring Every Day, Incorporated, Lexington, KY (US)

(72) Inventor: Franky Lydale Minnifield, Lexington, KY (US)

(73) Assignee: Measuring Every Day, Incorporated, Lexington, KY (US)

( * ) Notice: Subject to any disclaimer, the term of this patent is extended or adjusted under 35 U.S.C. 154(b) by 156 days.

(21) Appl. No.: 15/581,656

(22) Filed: Apr. 28, 2017

Related U.S. Application Data

(60) Provisional application No. 62/329,304, filed on Apr. 29, 2016.

(51) Int. Cl.
- *A61B 5/107* (2006.01)
- *A61B 5/11* (2006.01)
- *A61B 5/00* (2006.01)

(52) U.S. Cl.
CPC .......... *A61B 5/1121* (2013.01); *A61B 5/1072* (2013.01); *A61B 5/4585* (2013.01)

(58) Field of Classification Search
None
See application file for complete search history.

(56) References Cited

U.S. PATENT DOCUMENTS

| | | |
|---|---|---|
| 4,583,555 A | 4/1986 | Malcom et al. |
| 4,699,376 A | 10/1987 | Mattox et al. |
| 6,436,058 B1 | 8/2002 | Krahner et al. |
| 7,785,232 B2 | 8/2010 | Cole et al. |
| 8,282,579 B2 | 10/2012 | Bright et al. |
| 8,341,850 B2 | 1/2013 | Merchant |
| 2006/0064044 A1 | 3/2006 | Schmehl |
| 2007/0043308 A1 | 2/2007 | Lee |
| 2008/0132818 A1 | 6/2008 | Livorsi |
| 2012/0226199 A1 | 9/2012 | Nouveau |
| 2016/0000369 A1 | 1/2016 | Minnifield |

FOREIGN PATENT DOCUMENTS

| | | |
|---|---|---|
| WO | 03/094729 A1 | 11/2003 |

OTHER PUBLICATIONS

Rehabilitation Knee Stretch Device for Knee Pain and Meniscus Injuries, www.mendmyknee.com/knee-pain/knee-joint-rehabilitation-therapy-device.php (downloaded Jan. 20, 2014).

*Primary Examiner* — Eric F Winakur
*Assistant Examiner* — Marjan Fardanesh
(74) *Attorney, Agent, or Firm* — Sites & Harbison, PLLC; David W. Nagle, Jr.

(57) ABSTRACT

A measurement device for assessing knee movement, comprises: an elongated base member; a moveable member configured for movement along and relative to the elongated base member to provide a first assessment of knee movement; and an auxiliary measuring component mounted to the moveable member to provide a second assessment of knee movement, said auxiliary measuring component including (i) a first arm having a first end and a second end opposite the first end, (ii) a second arm having a first end and a second end opposite the first end, (iii) wherein second end of the first arm is pivotally connected to the second end of the second arm, such that the first arm rotates relative to the second arm, and (iv) wherein the second assessment of knee movement is based on the relative positioning of the first arm relative to the second arm.

13 Claims, 5 Drawing Sheets

MEASUREMENT DEVICE FOR ASSESSING KNEE MOVEMENT

CROSS-REFERENCE TO RELATED APPLICATIONS

The present application claims priority to U.S. Patent Application Ser. No. 62/329,304 filed on Apr. 29, 2016, the entire disclosure of which is incorporated herein by reference.

BACKGROUND OF THE INVENTION

The present invention relates to a measurement device for assessing knee movement, for example, prior to or after a knee surgery or a knee replacement.

Knee-related injuries are one of the most common injuries in sports. Many knee injuries result in a ruptured or torn anterior cruciate ligament (ACL), one of the four major ligaments of the knee. Injury to the ACL is often remedied by reconstructive surgery, followed by several months of physical therapy and rehabilitation. One of the biggest factors that determines whether a patient achieves full recovery is adherence to physical therapy schedules and rehabilitation exercises. Many of these exercises focus on restoring the range-of-motion of the knee. So, such exercises require constant measurement of the range-of-motion of the knee and monitoring of progress made during rehabilitation.

Although there are some complicated devices that exist in the art for measuring the range of motion of a knee, such as goniometers, most are complex mechanical or electromechanical devices that can only be used in a clinical setting with the assistance of a therapist.

Thus, in U.S. Patent Publication No. 2016/0000369 (which is incorporated herein by reference), a measurement device is described that generally comprises: an elongated base member; a moveable (or sliding) member configured for movement along and relative to the elongated base member; and indicia on an upper surface of the elongated base member to reflect the relative position of the moveable member with respect to the elongated base member.

As described in in U.S. Patent Publication No. 2016/0000369, the moveable member is configured for movement along and relative to the elongated base member. To measure knee flexion, a patient sits down and positions his or her leg on the measurement device in a starting position with the heel of the patient's foot positioned on the elongated base member. The patient begins bending his or her knee, such that the foot slides along the upper surface of the elongated base member. The moveable member is either pushed back by the foot as it slides along the upper surface of the elongated base member, or the moveable member is manually slid along the upper surface of the elongated base member as the patient bends his or her knee. Based on the indicia on the upper surface of the elongated base member, the patient is provided with a ready visual indication of how far the knee can be bent.

SUMMARY OF THE INVENTION

The present invention is a measurement device for assessing knee movement.

A measurement device made in accordance with the present invention includes: an elongated base member; a moveable (or sliding) member configured for movement along and relative to the elongated base member; and an auxiliary (or secondary) measuring component for assessing knee movement.

In some embodiments, indicia are provided on an upper surface of the elongated base member to reflect the relative position of the moveable member with respect to the elongated base member.

In some embodiments, the moveable member houses: a (i) sensor for determining the relative position of the moveable member with respect to the elongated base member; (ii) a microprocessor for receiving input from the sensor; and (iii) a display unit in communication with the microprocessor which receives and displays information regarding the relative position of the moveable member with respect to the elongated base member.

As mentioned above, a measurement device made in accordance with the present invention also includes an auxiliary (or secondary) measuring component for assessing knee movement. Specifically, the auxiliary measuring component includes a first arm and a second arm. The first arm has a first end and a second end opposite the first end. The second arm also has a first end and a second end opposite the first end. The respective second ends of the first and second arms each define a central hole, such that the second ends of the first and second arms are placed into registry with one another, with a pin passing through the respective central holes to create a pin connection. Thus, the first arm can pivot and rotate relative to the second arm.

The auxiliary measuring component is mounted to the moveable member. When so mounted to the moveable member, the position of the second arm of the auxiliary measuring component is substantially fixed, while the first arm can pivot and rotate relative to the second arm. Indicia are provided on the front surfaces of both second ends of the first and second arms, thus providing a ready visual indication of the relative positioning of the first arm relative to the second arm.

In use, the auxiliary measuring component is mounted to the moveable member. A patient sits down and positions his leg on the elongated base member of the measurement device and attempts to straighten his leg (i.e., achieve maximum flexion) with his knee above the moveable member. The first arm of the auxiliary measuring component is then rotated until the first end of the first arm contacts the underside of the knee. Referring to the indicia on the front surfaces of the second ends of the first and second arms, the relative positioning of the first arm relative to the second arm is noted and recorded. From this information, a calculation of the angular measurement of the knee of the patient at maximum flexion can be made. The auxiliary measuring component thus provides a simple and accurate means of measuring the degree of flexion in the patient's knee.

DETAILED DESCRIPTION OF THE INVENTION

Figure 1:
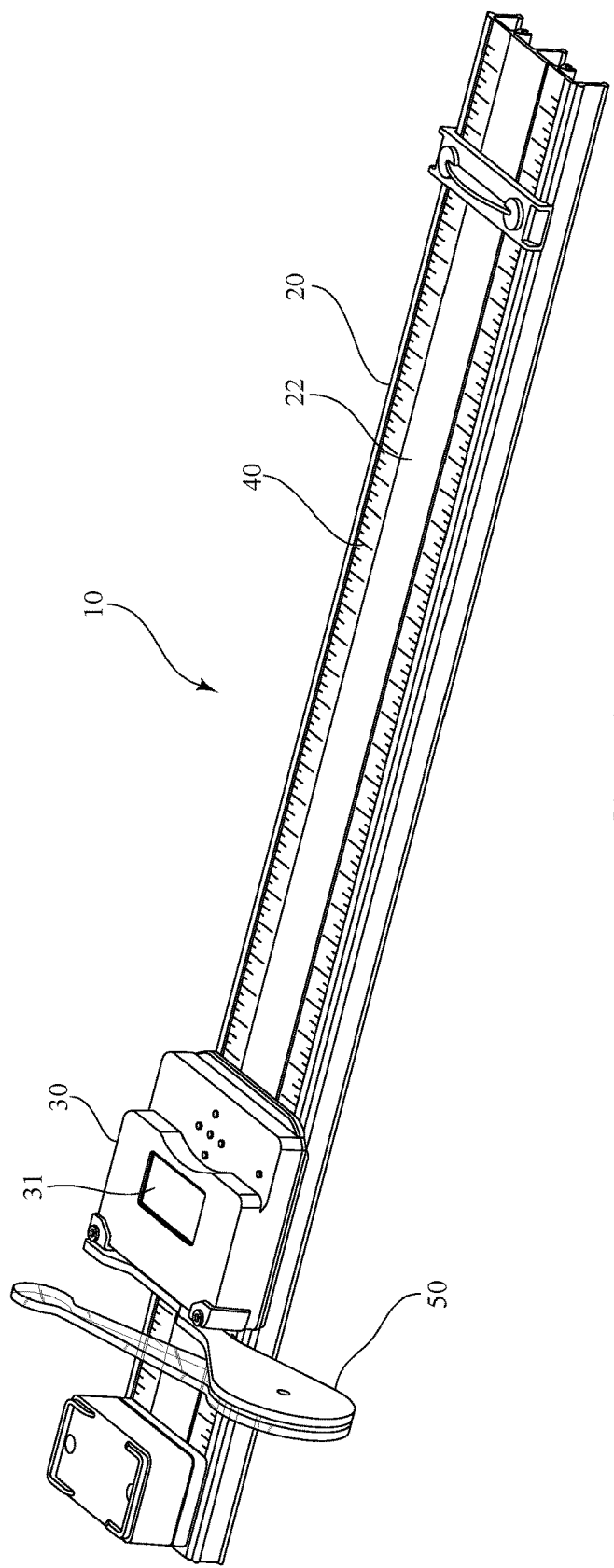
FIG. 1 is a perspective view of an exemplary measurement device for assessing knee movement made in accordance with the present invention.

The present invention is a measurement device for assessing knee movement.

As shown in FIGS. 1-4, similar to the measurement device described in U.S. Patent Publication No. 2016/0000369, an exemplary measurement device 10 made in accordance with the present invention includes: an elongated base member 20; and a moveable (or sliding) member 30 configured for movement along and relative to the elongated base member 20. In this exemplary embodiment, the moveable member 30 also houses: a (i) sensor (not shown) for determining the relative position of the moveable member 30 with respect to the elongated base member 20; (ii) a microprocessor (not shown) for receiving input from the sensor; and (iii) a display unit 31 in communication with the microprocessor which receives and displays information regarding the relative position of the moveable member 30 with respect to the elongated base member 20. Thus, like the measurement device described in U.S. Patent Publication No. 2016/0000369, the measurement device 10 allows the patient or attending therapist to be provided with a ready visual indication of how far the knee can be bent.

Alternatively, instead of using an electronic display, as in U.S. Patent Publication No. 2016/0000369, indicia 40 are also provided on an upper surface 22 of the elongated base member 20 to reflect the relative position of the moveable member 30 with respect to the elongated base member 20.

Figure 2:
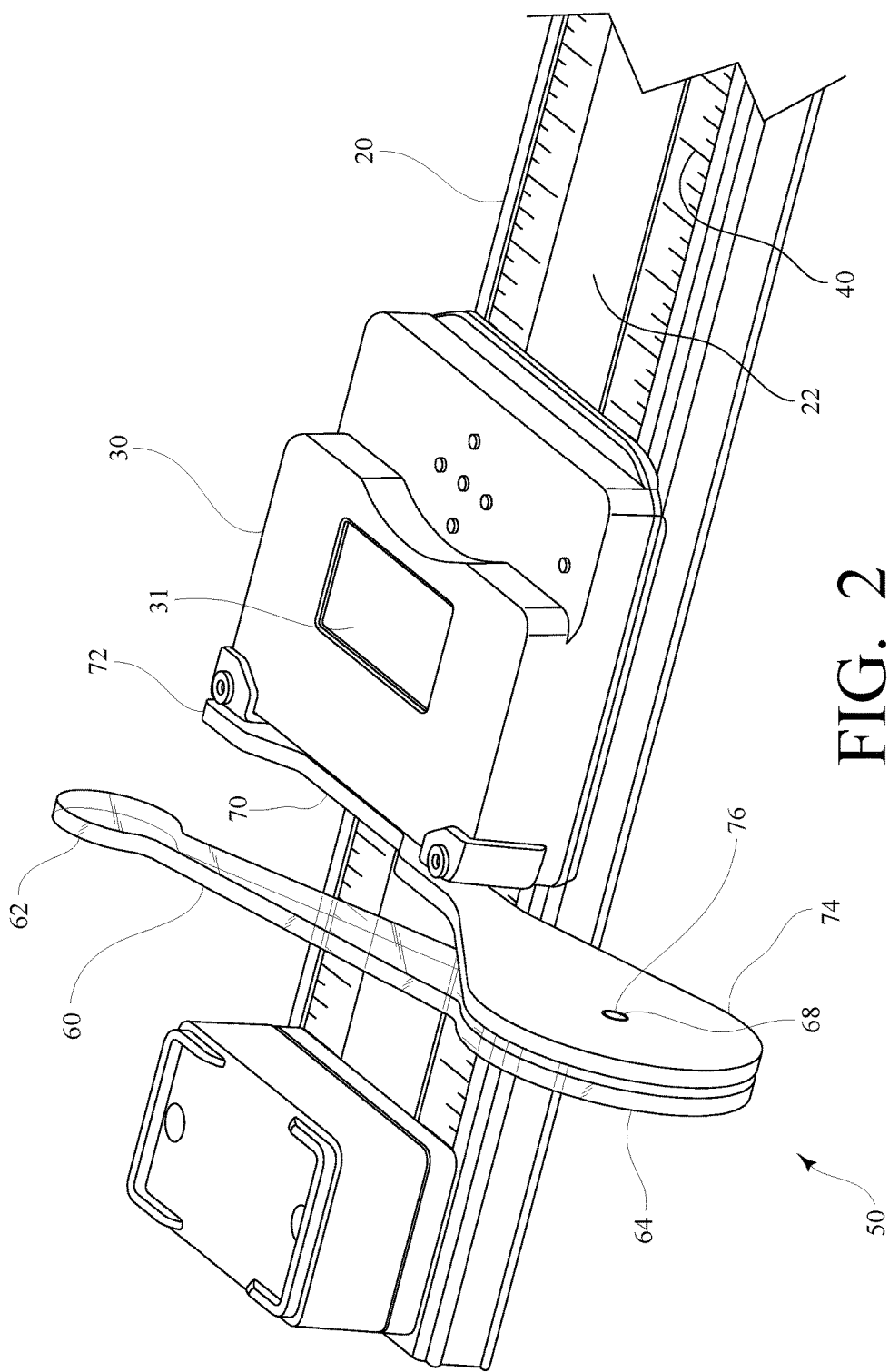
FIG. 2 is an enlarged perspective view of the exemplary measurement device of FIG. 1.
Figure 3:
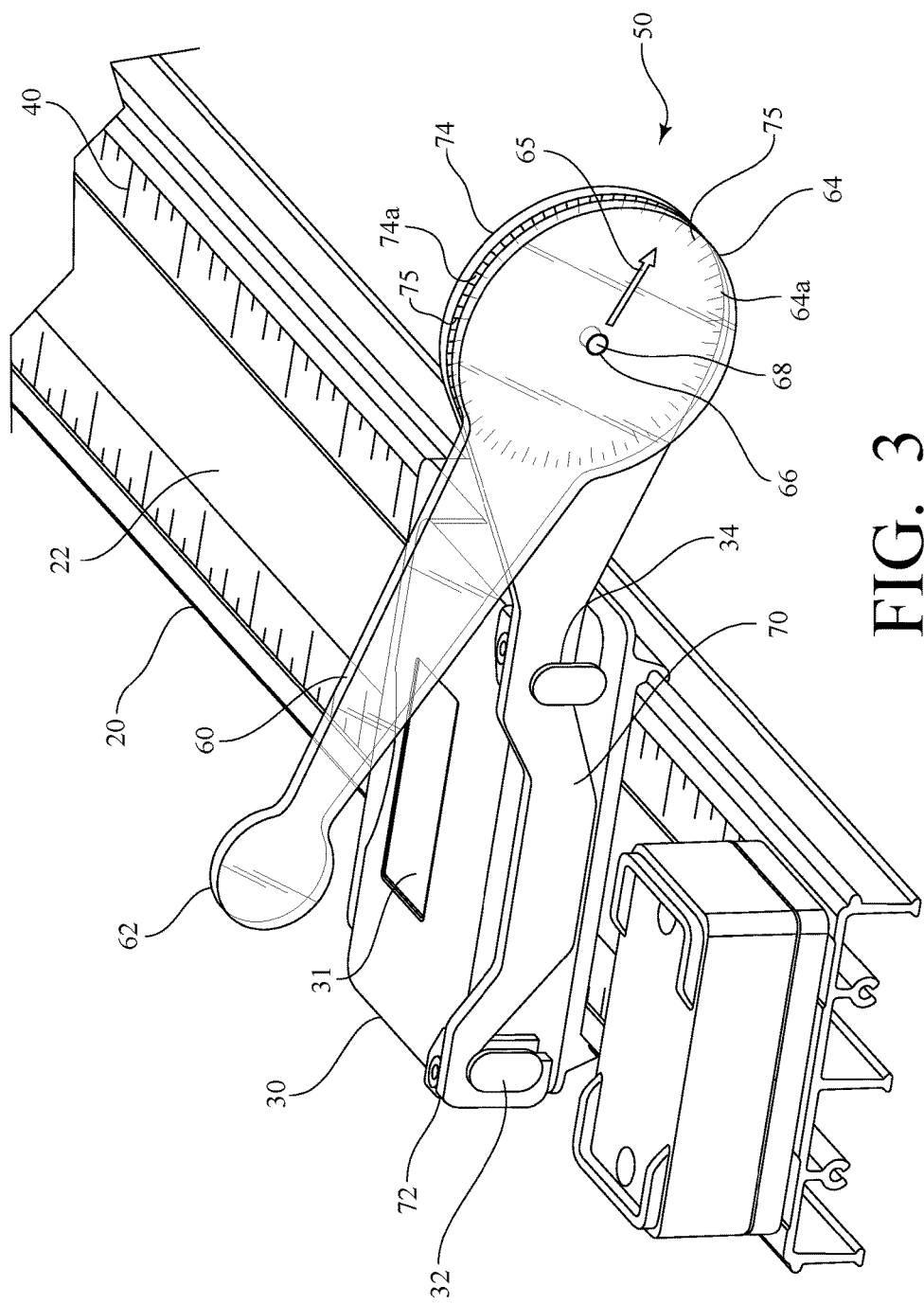
FIG. 3 is another enlarged perspective view of the exemplary measurement device of FIG. 1.
Figure 4:
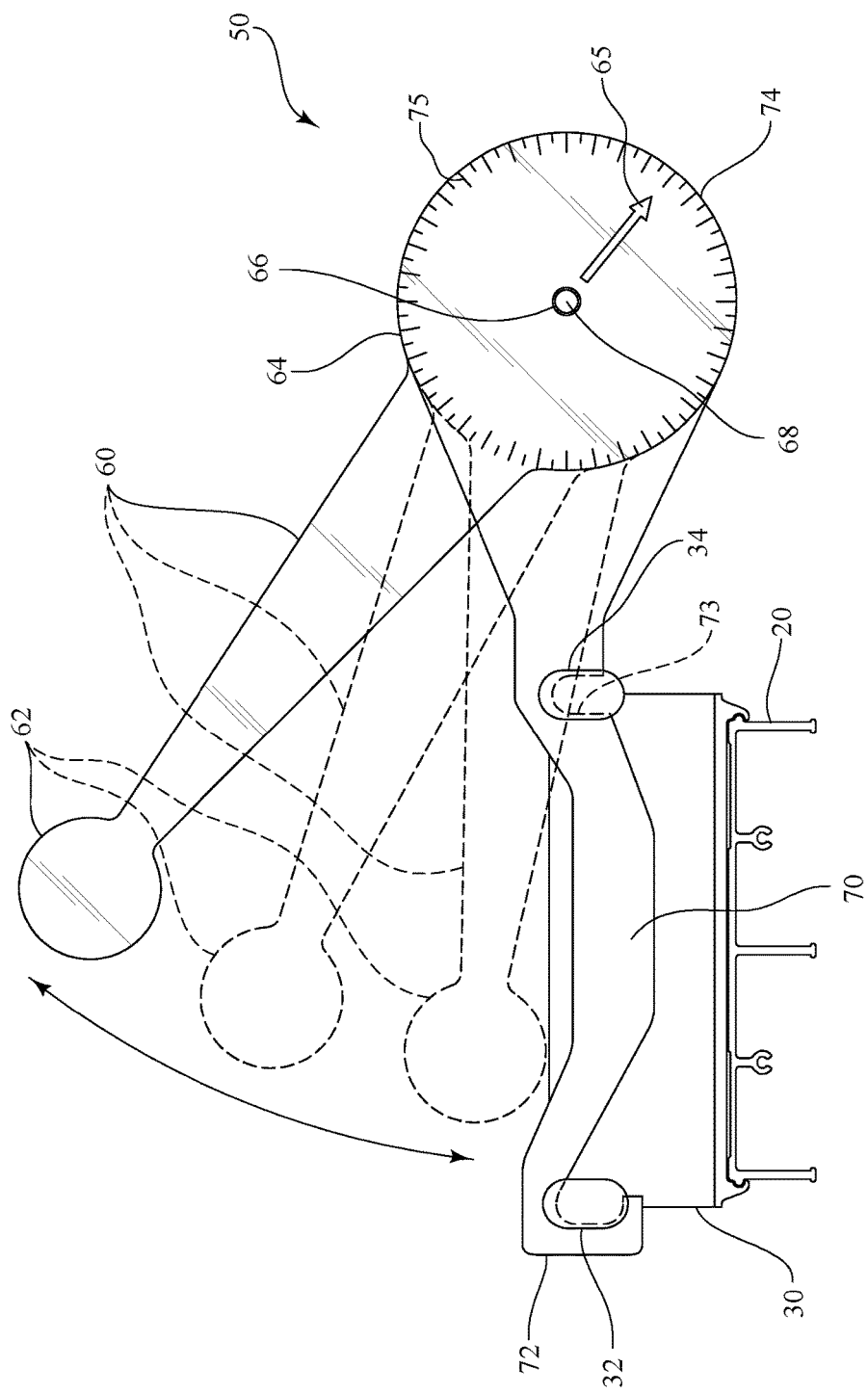
FIG. 4 is a front view of the exemplary measurement device of FIG. 1, illustrating rotation of the second arm of the auxiliary measuring component relative to the first arm.

Referring now to FIGS. 2-4, the exemplary measurement device 10 also includes an auxiliary (or secondary) measuring component 50 for assessing knee movement. Specifically, the auxiliary measuring component 50 includes a first arm 60 and a second arm 70. The first arm 60 has a first end 62 and a second end 64 opposite the first end 62. In this exemplary embodiment, the first end 62 of the first arm 60 has a generally circular shape, and the second end 64 of the first arm 60 also has a generally circular shape, but with a much larger diameter. The second arm 70 also has a first end 72 and a second end 74 opposite the first end 72. In this exemplary embodiment, the first end 72 of the second arm 70 terminates in a hook-like shape, the importance of which will be described below. The second end 74 of the second arm 70 has a generally circular shape that generally corresponds to that of the second end 64 of the first arm 60. The respective second ends 64, 74 of the first and second arms 60, 70 each define a central hole 66, 76, such that the second ends 64, 74 of the first and second arms 60, 70 are placed into registry with one another, with a pin 68 passing through the respective central holes 66, 76 to create a pin connection. Thus, the first arm 60 can pivot and rotate relative to the second arm 70.

Referring still to FIGS. 2-4, the auxiliary measuring component 50 is selectively mounted to the moveable member 30. Specifically, in this exemplary embodiment, the moveable member 30 includes a first bracket 32 and a second bracket 34 that each extend from a lateral surface of the moveable member 30. As described above, the first end 72 of the second arm 70 terminates in a hook-like shape, which, when the auxiliary measuring component 50 is mounted to the moveable member 30, engages the first bracket 32, while the second bracket 34 supports an intermediate portion of the second arm 70. As shown in FIG. 4, in this exemplary embodiment, there is a notch 73 defined in the intermediate portion of the second arm 70 that engages the bracket 34. Thus, when the auxiliary measuring component 50 is mounted to the moveable member 30, the position of the second arm 70 is substantially fixed, while the first arm 60 can pivot and rotate relative to the second arm 70.

As best shown in FIGS. 3 and 4, indicia are provided on the front surfaces 64a, 74a of both second ends 64, 74 of the first and second arms 60, 70. Specifically, in this exemplary embodiment, an arrow 65 is illustrated on the front surface 64a of the second end 64 of the first arm 60. Furthermore, the first arm 60 is preferably comprised of a translucent material, at least in the vicinity of the arrow 65. Corresponding indicia 75 on the front surface 74a of the second end 74 of the second arm 70 can thus be viewed through the second end 64 of the first arm 60. In other words, the arrow 65 is effectively laid over the corresponding indicia 75 on the front surface 74a of the second end 74 of the second arm 70, thus providing a ready visual indication of the relative positioning of the first arm 60 relative to the second arm 70.

Alternatively, rather than manufacturing the first arm 60 or a portion thereof from a translucent material, the second end 64 of the first arm 60 may be constructed to have a diameter slightly smaller than that of the second end 74 of the second arm, such that the corresponding indicia 75 can be viewed along the periphery of the second end 64 of the first arm 60 to provide the visual indication of the relative positioning of the first arm 60 relative to the second arm 70.

Alternatively, rather than manufacturing the first arm 60 or a portion thereof from a translucent material, the second end 64 of first arm 60 may be provided with an opening or "window" (not shown) through which the corresponding indicia 75 can be viewed to provide the visual indication of the relative positioning of the first arm 60 relative to the second arm 70.

Figure 5A:
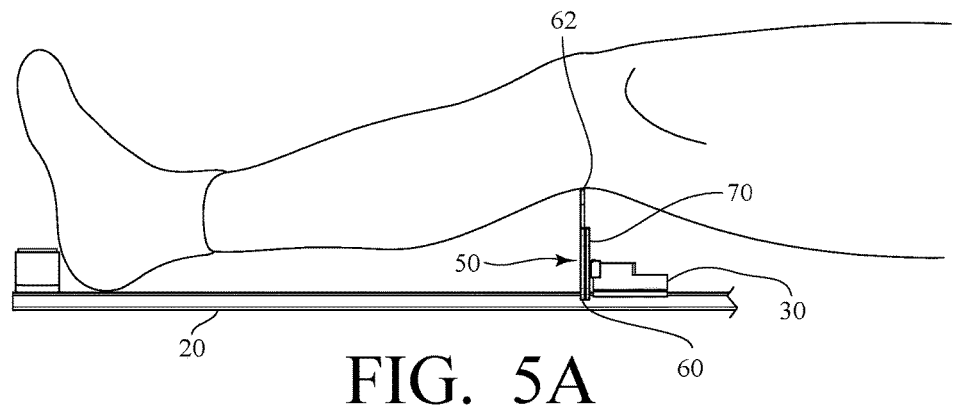
FIG. 5A is a side view of the exemplary measurement device of FIG. 1, illustrating use of the auxiliary measuring component.
Figure 5B:
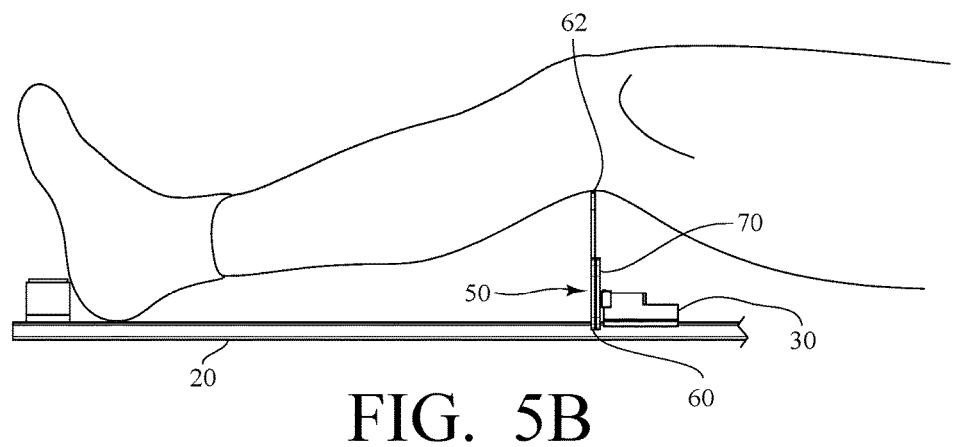
FIG. 5B is another side view of the exemplary measurement device of FIG. 1, again illustrating use of the auxiliary measuring component.
Figure 5C:
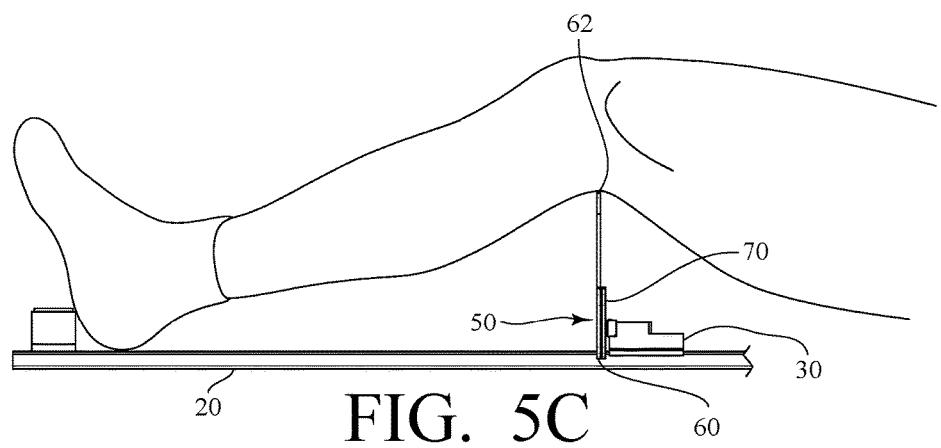
FIG. 5C is yet another side view of the exemplary measurement device of FIG. 1, again illustrating use of the auxiliary measuring component.

Referring now to FIGS. 5A-5C, in use, the auxiliary measuring component 50 is mounted to the moveable member 30. A patient sits down and positions his leg on the elongated base member 20 of the measurement device 10 and attempts to straighten his leg (i.e., achieve maximum flexion) with his knee above the moveable member 30. The first arm 60 of the auxiliary measuring component 50 is then rotated until the first end 62 of the first arm 60 contacts the underside of the knee. Referring to the indicia 65, 75 on the front surfaces 64a, 74a of the second ends 64, 74 (see FIGS. 3 and 4) of the first and second arms 60, 70, the relative positioning of the first arm 60 relative to the second arm 70 is noted and recorded. From this information, a calculation of the angular measurement of the knee of the patient at maximum flexion can be made. The auxiliary measuring component 50 thus provides a simple and accurate means of measuring the degree of flexion in the patient's knee.

Furthermore, it should be recognized that the auxiliary measuring component 50 can be detached from the moveable member 30 and used as a measurement device separate and apart from the elongated base member 20 and the moveable member 30.

One of ordinary skill in the art will recognize that additional embodiments are also possible without departing from the teachings of the present invention. This detailed description, and particularly the specific details of the exemplary embodiment disclosed therein, is given primarily for clarity of understanding, and no unnecessary limitations are to be understood therefrom, for modifications will become obvious to those skilled in the art upon reading this disclosure and may be made without departing from the spirit or scope of the invention.

What is claimed is:

1. A measurement device for assessing movement of a knee, comprising:
    an elongated base member;
    a moveable member configured for movement along and relative to the elongated base member to provide a first assessment of knee movement; and
    an auxiliary measuring component mounted to the moveable member to provide a second assessment of knee movement, said auxiliary measuring component including (i) a first arm having a first end and a second end opposite the first end, (ii) a second arm having a first end and a second end opposite the first end, (iii) wherein the second end of the first arm is pivotally connected to the second end of the second arm, such that the first arm rotates relative to the second arm, and (iv) wherein the second assessment of knee movement is based on the relative positioning of the first arm relative to the second arm;
    wherein, in use, with a leg of a patient positioned on the elongated base member of the measurement device, the first arm of the auxiliary measuring component is rotated until the first end of the first arm contacts an underside of the knee of the patient, and the second assessment of knee movement is then based on the relative positioning of the first arm relative to the second arm.

2. The measurement device as recited in claim 1, wherein the first end of the first arm of the auxiliary measuring component has a generally circular shape.

3. The measurement device as recited in claim 1, wherein, with respect to the auxiliary measuring component, the second end of the first arm and the second end of the second arm each define a central hole, with the respective second ends of the first arm and the second arm placed into registry with one another with a pin passing through the respective central holes to create a pin connection.

4. The measurement device as recited in claim 3, when the second end of the first arm and the second end of the second arm of the auxiliary measuring component each have a generally circular shape.

5. The measurement device as recited in claim 3, wherein indicia are provided on a front surface of the second end of the first arm of the auxiliary measuring component, and corresponding indicia are provided on a front surface of the second end of the second arm of the auxiliary measuring component, thus providing a ready visual indication of the relative positioning of the first arm relative to the second arm.

6. The measurement device as recited in claim 5, wherein the indicia provided on the front surface of the second end of the first arm of the auxiliary measuring component is an arrow.

7. The measurement device as recited in claim 5, wherein at least a portion of the first arm of the auxiliary measuring component is comprised of a translucent material, such that the indicia on the front surface of the second end of the first arm of the auxiliary measuring component is effectively laid over the corresponding indicia on the front surface of the second end of the second arm, thus providing the ready visual indication of the relative positioning of the first arm relative to the second arm.

8. The measurement device as recited in claim 1, wherein the moveable member includes one or more brackets that extend from a lateral surface of the moveable member and are configured to support the auxiliary measuring component.

9. The measurement device as recited in claim 1, wherein the moveable member includes a first bracket and a second bracket that each extend from a lateral surface of the moveable member and are configured to support the auxiliary measuring component.

10. The measurement device as recited in claim 9, wherein the first end of the second arm terminates in a hook-like shape, which, when the auxiliary measuring component is mounted to the moveable member, engages the first bracket, while the second bracket supports an intermediate portion of the second arm of the auxiliary measuring component.

11. A measurement device for assessing movement of a knee, comprising:
    an elongated base member;
    a moveable member configured for movement along and relative to the elongated base member to provide a first assessment of knee movement; and
    an auxiliary measuring component mounted to the moveable member to provide a second assessment of knee movement, said auxiliary measuring component including (i) a first arm having a first end and a second end opposite the first end, (ii) a second arm having a first end and a second end opposite the first end, (iii) wherein the second end of the first arm is pivotally connected to the second end of the second arm, such that the first arm rotates relative to the second arm, and (iv) wherein indicia are provided on a front surface of the second end of the first arm, and corresponding indicia are provided on a front surface of the second end of the second arm, thus providing a ready visual indication of the relative positioning of the first arm relative to the second arm;
    wherein, in use, with a leg of a patient positioned on the elongated base member of the measurement device, the first arm of the auxiliary measuring component is rotated until the first end of the first arm contacts an underside of the knee of the patient, and the second assessment of knee movement is then based on the relative positioning of the first arm relative to the second arm.

12. The measurement device as recited in claim 1, wherein the first arm of the auxiliary measuring component rotates relative to the second arm about an axis that is substantially parallel to a longitudinal axis of the elongated base member.

13. The measurement device as recited in claim 11, wherein the first arm of the auxiliary measuring component rotates relative to the second arm about an axis that is substantially parallel to a longitudinal axis of the elongated base member.

* * * * *